United States Patent [19]
Vacher et al.

[11] Patent Number: 6,096,316
[45] Date of Patent: Aug. 1, 2000

[54] COMPOSITION FOR LIMITING AND ATTENUATING THE VISIBLE SYMPTOMS OF NATURAL OR ACCIDENTAL AGEING OF THE SKIN

[75] Inventors: Anne-Marie Vacher, Le Chesnay; Marie-Claire Fritsch, Paris, both of France

[73] Assignee: Lanatech Laboratories Nature et Technique, France

[21] Appl. No.: 09/101,527

[22] PCT Filed: Nov. 10, 1997

[86] PCT No.: PCT/FR97/02017

§ 371 Date: Nov. 24, 1998

§ 102(e) Date: Nov. 24, 1998

[87] PCT Pub. No.: WO98/20851

PCT Pub. Date: May 22, 1998

[30] Foreign Application Priority Data

Nov. 14, 1996 [FR] France .................................. 96 14121

[51] Int. Cl.[7] ............................ A61K 35/78; A61K 31/35
[52] U.S. Cl. ........................ 424/195.1; 514/26; 514/457; 514/456; 514/455; 514/451; 514/460
[58] Field of Search ........................ 424/180, 63, 195.1; 514/783, 460, 26, 457, 455, 451, 456

[56] References Cited

U.S. PATENT DOCUMENTS

| | | | |
|---|---|---|---|
| 4,146,615 | 3/1979 | Fauran et al. ........................... | 424/195 |
| 4,335,113 | 6/1982 | Combier et al. ......................... | 424/180 |
| 5,093,109 | 3/1992 | Mausner ................................... | 424/63 |

FOREIGN PATENT DOCUMENTS

| | | | |
|---|---|---|---|
| 2618071 | 1/1989 | France . | |
| 2618071A | 1/1989 | France ............................. | A61K 7/48 |
| 2702376A | 3/1993 | France ............................. | A61K 35/78 |
| 2801186 | 7/1978 | Germany . | |
| 3878169G | 3/1993 | Germany ....................... | A61K 35/78 |

OTHER PUBLICATIONS

D. Honore–Thorez—Jrnl of Pharmacology, Liege, Belgium, 1985, vol. 40, issue 5, pp. 323–331—Abstract Only.

T.Brasseur, L.Angenot, J.Pincemail, C.Deby—Plant.Med.Phytogher, 1987, vol. 21, issue 2, pp. 131–137.—Abstract Only.

*Primary Examiner*—William R. A. Jarvis
*Assistant Examiner*—Vickie Kim
*Attorney, Agent, or Firm*—William A. Drucker

[57] ABSTRACT

The composition is characterized in that it contains an extract of Chrysanthellum indicum with low concentration comprising 0.0001% to 0.05% of equivalent dry extract of Chrysanthellum indicum. It is both applicable to natural ageing and to phenomena of accidental ageing of the skin caused by the numerous assaults to which the skin is subjected daily.

21 Claims, No Drawings

COMPOSITION FOR LIMITING AND ATTENUATING THE VISIBLE SYMPTOMS OF NATURAL OR ACCIDENTAL AGEING OF THE SKIN

This application is a 371 of PCT/FR97/02017 filed on Jan. 10, 1997.

BACKGROUND OF THE INVENTION

1. Field of the Invention

The present invention relates to a composition which is used to for limiting and attenuating the visible symptoms of natural or accidental ageing of the skin. It applies both to natural ageing (anti-ageing action) and to phenomena of accidental ageing of the skin due to the many attacking factors to which the skin is subjected daily, in particular those caused by solar radiation (antisun products and after-sun products).

In general, it is known that ageing is an unavoidable phenomenon, but certain factors can accelerate the process. It is known that the ultraviolet radiation of light adversely affects the normal functions of the skin and that prolonged exposure to solar radiation contributes towards ageing and to the induction of skin cancers. Free radicals are the main agents incriminated in these adverse changes.

Free radicals are corrosive particles which have a free electron, of great chemical reactivity, and are thus particularly unstable.

They are generated by ionizing radiation, ultraviolet radiation and even visible sunlight, but they are also derived from the metabolic and enzymatic reactions which take place in the body. These reactions take place, for example, during cell respiration, in the mitochondria, or during the synthesis of prostaglandins, in the course of the inflammation process, or alternatively during phagocytosis.

A free radical can form according to two types of chemical process:

homolytic cleavage of a single chemical bond between two atoms in a molecule, each taking one electron from the bond with it:

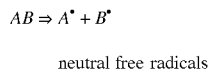

neutral free radicals transfer of an electron (redox reaction) between two molecules (an oxidizing agent and a reducing agent) which gives rise to two charged radicals:

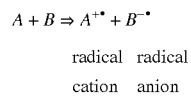

radical radical
cation anion

The most common reaction resulting from having free radicals in solution is the stripping of a hydrogen atom from a substrate present in the medium, which leads to the formation of a new free radical:

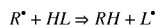

The radical-mediated attack initiates chain reactions which stop only when two free radicals mutually inactivate themselves.

Lipid peroxidation (lipoperoxidation) is a typical case of a radically-induced chain reaction.

The oxidation of membrane lipids results in the formation of lipoperoxides, which decompose into various fragmentation products, some of which are highly corrosive.

One of the most important and most corrosive fragmentation products is an aldehyde, malondialdehyde (MDA). Since this molecule bears two free radicals, it exhibits formidable toxicity by bridging across proteins, intracellular lipids and DNA.

In the toxicity of free radicals towards biological systems, oxygen-derived reactive species occupy a predominant position.

The main radical species involved in biological processes are the following:

| | |
|---|---|
| $^1O_2$ | singlet oxygen |
| $O_2^{\bullet-}$ | superoxide anion radical which induces the formation of a much more reactive radical: |
| $OH^\bullet$ | hydroxyl radical, very powerful oxidizing agent |
| $HOO^\bullet$ | perhydroxyl radical (protonated form of $O_2^{\bullet-}$) |
| $LO^\bullet$ | lipid alkoxyl radical |
| $LOO^\bullet$ | lipid peroxyl radical |

(L = polyunsaturated phospholipid group)

The free radicals and the cascade of chain reactions which they generate in the body play a very important role in the process of ageing of the skin.

Their destructive action on membrane lipids results in the slow death of cells.

They also attack the genetic patrimony of cells: DNA and RNA, which are essential molecules for protein synthesis reactions.

Lastly, they degrade proteins, in particular collagen fibres and elastic fibres, the functional characteristics of which are severely impaired.

The results of all this are damaged, prematurely aged skin.

Now, cell metabolism (in particular respiration) generates free radicals. This is an entirely normal phenomenon which cells are capable of combating since they are equipped with suitable means of defence.

In certain circumstances, this harmonious equilibrium can be broken. The natural protection system of the cell is then no longer sufficiently effective. Many causes trigger a breakdown in the equilibrium of cells with respect to free radicals:

poor food hygiene prolonged and repeated exposure of the body to ionizing radiation (X-rays, UV rays, excessive sunbathing)

poor use of medicaments and abuse of tobacco or alcohol pollution stress, which is an indirect promoter of free radicals, etc.

Various means exist in cells for opposing and neutralizing free radicals: protective agents, enzymes (superoxide dismutase, glutathione peroxidase and catalase), certain trace elements (zinc, selenium) and vitamins (vitamins A–C and especially E).

However, a certain number of radicals escape this natural defence. This can, in the long run, lead to a cumulative phenomenon which arises in the process of senile involution and wear.

2. Description of the Prior Art

In order to combat this phenomenon, anti-radical compounds have already been proposed which help the natural defence systems of cells in order to allow the body to recover harmonious functioning. These compounds, just like the molecules naturally present in the skin, form with free radicals, on account of chemical, physicochemical and electrochemical affinities that are much greater for free radicals than for the membrane structures, stable, non-radical products.

Depending on their nature, the anti-radical substances block the chain reaction at various stages, thus more or less rapidly stopping the radical-mediated attack. In this way, the lipid membranes are preserved.

It is also recalled that, in living beings, cells are affected by various types of oxidative reaction, including the following two reactions:

reactions resulting in the production of the hydroxyl radical OH., those derived from haems, such as free haemoglobin, which produces oxoferryl-type radicals.

Moreover, it is known that the content of ATP (adenosine triphosphate, the main energetic substrate of cells) in human epidermal keratinocytes partly reflects the energetic state of cells: ATP, the molecule for transferring and storing energy, is essential for cell metabolism.

It has been observed during experiments that the content of ATP in keratinocytes falls significantly after exposure to radiation such as, for example, ultraviolet radiation (UVB).

OBJECT OF THE INVENTION

The subject of the invention is thus, more particularly, a composition which:

has very good anti-radical properties, so as to obtain an anti-ageing action for both natural and accidental ageing, affords effective protection against the reactions which result in the production of OH. radicals or oxoferryl-type radicals, reduces the fall in the ATP content of keratinocytes after irradiation, so as to obtain a repairing effect.

SUMMARY OF THE INVENTION

In order to obtain these results, it is proposed to use the properties of Chrysanthellum indicum.

Chrysanthellum indicum, also known as Chrysanthellum americanum or procumbens, which is registered on the list of medicinal plants in the pharmacopoeia, in particular for its hepatoprotective-hepatostimulating, anti-lithiasic, anti-oedemal and anti-inflammatory actions, contains phenylpropenic acids, flavonoids and saponosides. It conjugates saponosides and flavonoids in an unusual manner in the plant world, with an exceptional richness in flavonoids since it combines a flavone, an aurone, a chalcone and two flavanones, this combination also being relatively uncommon in the plant kingdom.

This entirely surprising combination gives rise to the many virtues of Chrysanthellum indicum, which is a remedy used for the treatment of various complaints, of digestive, circulatory, etc. origin, such as:

hepatitis, colopathies, ictero-haemorrhagic syndromes, urinary and bile lithiases, cardiovascular and circulatory pathologies, etc.

In particular, Chrysanthellum indicum is recommended in the case of bile insufficiency, attacks of hepatitis, alcoholic intoxication, salivary, renal or bile lithiases, enterocolitic disorders, vascular complaints and disruption of lipid metabolism.

The studies reported show that chrysanthellum-based treatments are carried out orally (herbal tea, plant extracts in syrup form, in gelatin capsule form, etc.) or intraperitoneally, but in no case is it carried out topically.

The only document reported concerning the value of Chrysanthellum indicum in fields other than the strictly medical field is French patent No. 2,618,071, which proposes cosmetic and dermatological compositions containing between 1% and 10% by weight of chrysanthellum dry extract for applications such as shampoos and hair lotions, dermal emulsions, body milks and lipsticks, or even cosmetic compositions in aerosol form.

Besides the fact that that document does not mention the prevention of ageing of the skin, the concentrations recommended for use lead to totally inappropriate products, which are even incompatible with normal cosmetic use since, at these concentrations, emulsions for topical use have, in particular:

A dark brown coloration which leads to intense mustard-yellow staining of the skin to be treated, as well as of the fingers used to apply the product. The high intensity of this staining is attenuated by rinsing, but a dark yellow coloration remains after washing.

Poor stability over time: from 24 hours onwards, concentration of water in the bottom of the container and considerable release of oil at the surface are observed.

A strong odour of plant extract.

It turns out that, even if it were hypothetically possible to formulate a sufficiently stable product with such concentrations of chrysanthellum dry extracts, the coloration of this product would remain a major problem:

Excessively intense colour not at all in keeping with what consumers using cosmetic products will generally find acceptable.

Product acting essentially as a dye: the skin and the nails are unavoidably stained a more or less pronounced yellow. Similarly, tissues which come into contact with this product are indelibly stained a more or less pronounced yellow which turns to orange after washing with the usual detergents.

DESCRIPTION OF PREFERRED EMBODIMENTS

The aim of the invention is thus, more particularly, to develop a composition which can be administered topically, which uses the active principles of Chrysanthellum indicum for the purpose of for limiting and attenuating the visible symptoms of natural or accidental ageing, and which solves the problems both of coloration and of odour mentioned above.

The invention achieves this result by means of a composition comprising an extract of Chrysanthellum indicum at low concentration, containing from 0.0001% to 0.05%, i.e. 1 $\mu$g/ml to 500 $\mu$g/ml of dry extract equivalents, of Chrysanthellum indicum.

The results of the tests carried out show that, within this concentration range, contrary to all expectation, chrysanthellum exerts a powerful anti-radical effect and that, moreover, the problems of coloration, of odour and of stability are easily solved.

During these tests, the effects of a dry extract of Chrysanthellum indicum on the production of oxygen-containing free radicals were revealed using a chemical model consisting of a microemulsion of sodium linoleate as an aqueous solution, the hydroxyl radicals being produced by radiolysis of the water.

The oxoferryl radicals were generated by the contact of a haemoglobin solution with the microemulsion, which was treated with ultrasound beforehand in order to produce traces of lipoperoxides therein, which reacted with the haemoglobin triggering a chain-lipoper-oxidation.

In the two cases, the lipoperoxidation was followed by application of the property, exhibited by linoleic acid hydroperoxides, of cleaving to release pentane. The reactions proceeded in a closed system, and samples of gas were removed and injected into a gas chromatograph, allowing assaying of the pentane, the amount of which is proportional to the lipoperoxides formed. As an organic extract whose composition was unknown was involved (which does not allow the molarity to be calculated), the results were expressed as a percentage of pentane relative to controls free of the substance (in which a maximum peroxidation will take place). It is clear that the lowering in the production of pentane is proportional to the fall in lipoperoxidation reactions, and thus to the antioxidant efficacy of the test product.

The curve of inhibition of the test substance was compared with that of antioxidants of recognized efficacy, in this case uric acid as standard water-soluble antioxidant and BHT, which is liposoluble, for protecting polyunsaturated acids at a concentration of $10^{-3}$ M.

Evaluation of the product submitted:

The test substance: (dry extract of chrysanthellum) was dissolved in a phosphate buffer at pH 7.4. It is thus water-soluble, leaves no trace of insoluble product and gives a transparent solution.

This study made it possible to observe a very marked protective effect of the test substance, irrespective of the system used to produce the free radicals. This effect appears, surprisingly, at very low doses and is already perceptible at 0.0015 µg/ml.

The dry extract of chrysanthellum studied has noteworthy anti-hydroxyl efficacy, since the plant extracts conventionally studied cease to be active below 125 µg/ml. Its anti-oxoferryl effect is less effective, but still remains comparable with that of the most active plant extracts known as scavengers of this radical.

The in vitro study of the effect of the dry extract of Chrysanthellum indicum on human keratinocyte cultures which have been subjected to stress with UVB rays made it possible to reveal a repairing effect.

In this study, the cells were subjected to various doses of ultraviolet (UVB) irradiation.

This UVB radiation induces the formation of free radicals with harmful effects on cell metabolism.

After irradiation, the cells were incubated for 24 hours with the extract of chrysanthellum or the reference molecules (vitamin C and PABA, a UVB screening agent).

The ATP content of the keratinocytes is measured at the times T0 (before irradiation), T1 (after irradiation) and T2 (24 hours after irradiation=duration of incubation).

The keratinocyte ATP content evaluated immediately after irradiation (time T1) fell in all the cases featured. This decrease is accentuated at the times T2 in the case of the untreated control.

The effect of the test compound and of the reference molecules on the cell content of ATP was evaluated at time T2.

This study made it possible to observe that, at a concentration of 0.003%, the extract of Chrysanthellum indicum increases the cell content of ATP in the irradiated cells by a factor of 1.8 (relative to the untreated irradiated cells) at doses of 0.945 and 1.89 $J/cm^2$.

Chrysanthellum indicum allows keratinocytes damaged by UVB radiation to recover some of their initial level of ATP faster than untreated damaged keratinocytes.

It thus has an entirely positive effect on human keratinocyte cultures which have undergone a UVB stress.

This observation, made with low concentrations of active agent relative to those generally used in a formulation, is compatible with the concentrations used to obtain the "repairing effect" mentioned above.

It thus appears that, on account of its anti-radical and anti-lipoperoxidative action, the extract of Chrysanthellum indicum, in any form whatsoever (dry extract, glycolic solutions, etc.), is an agent for preventing ageing of the skin.

It attenuates the effects of time and the many attacking factors to which the skin is subjected daily, by neutralizing the free radicals produced by the body or by limiting their production (excessive production when the skin is subjected to situations of "cell stress").

Its use is particularly recommended for the formulation of daily care products for "anti-ageing" purposes, antisun products and after-sun products.

Examples of the formulation of compositions will be described below, by way of non-limiting examples.

EXAMPLE I

After-sun Gel

| A1 | Demineralized water | qs 100% |
|---|---|---|
| A2 | Glycerol | from 1 to 5%, preferably 3.00% |
| B1 | Acrylic gelling agent | from 0.1 to 1%, preferably 0.30% |
| C1 | Triethanolamine | from 0.1 to 1%, preferably 0.50% |
| D1 | Antimicrobial preserving agent | from 0.5 to 1%, preferably 0.55% |
| E1 | Plant oil or mineral oil | from 1 to 5%, preferably 2.00% |
| F1 | Fragrance | from 0.1 to 1%, preferably 0.15% |
| H1 | Extract of chrysanthellum contained in the composition as a solution in butylene glycol and water (i.e. from 0.0001% to 0.05% of dry extract of chrysanthellum) | from 0.005% to 2.5%, preferably 0.50% |

EXAMPLE II

Anti-radical cream

| A1 | Sorbitol stearate | from 1 to 2%, preferably 1.50% |
|---|---|---|
| A2 | Glyceryl stearate and polyethylene glycal-100 | from 2 to 5%, preferably 3.25% |
| A3 | Mineral oils and plant oils | from 10 to 20%, preferably 13.50% |
| B1 | Demineralized water | qs 100% |
| B2 | Propylene glycol | from 1 to 5%, preferably 2.50% |
| C1 | Acrylic gelling agent | from 0.1 to 1%, preferably 0.40% |
| D1 | Triethanolamine | from 0.1 to 1%, |

-continued

| | | |
|---|---|---|
| E1 | Antimicrobial preserving agent | preferably 0.40%<br>from 0.5 to 1%, preferably 0.80% |
| F1 | Fragrance | from 0.1 to 1%, preferably 0.15% |
| G1 | Gelling agent (for example such as Sepigel sold by the company SEPPIC) | from 0.1 to 2%, preferably 0.70% |
| H1 | Extract of chrysanthellum contained in the composition solution in butylene glycol and water (i.e. from 0.0001% to 0.05% of dry extract of chrysanthellum) | from 0.005% to 2.5%, preferably 1.00% |

EXAMPLE III

Antisun milk

| | | |
|---|---|---|
| A1 | Demineralized water | qs 100% |
| A2 | Titanium dioxide | from 0.1 to 2%, preferably 0.20% |
| A3 | Sorbitol | from 0.5 to 5%, preferably 1% |
| B1 | Triethanolamine | from 0.1 to 1%, preferably 0.30% |
| C1 | Glyceryl stearate and polyethylene glycol-100 | from 1 to 5%, preferably 2.00% |
| C2 | Glyceryl stearate | from 0.1 to 1%, preferably 0.30% |
| C3 | Stearic acid | from 0.5 to 5%, preferably 1.00% |
| C4 | Plant oils and mineral oils | from 5 to 15%, preferably 8.00% |
| C5 | Sunscreen (cinnamate) | from 0.5 to 10%, preferably 5.00% |
| C6 | Antioxidant | from 0.01 to 0.1%, preferably 0.07% |
| D1 | Acrylic gelling agent | from 0.1 to 1%, preferably 0.10% |
| E1 | Antimicrobial preserving agent | from 0.5 to 1%, preferably 0.80% |
| F1 | Fragrance | from 0.1 to 1%, preferably 0.40% |
| G1 | Extract of chrysanthellum as a solution in propylene glycol and water (i.e. from 0.0001% to 0.05% of dry extract of chrysanthellum) | for example 5.00% |

In these examples, the dry extract of Chrysanthellum indicum is obtained in a conventional manner by grinding the fresh or dry plant until a powder is obtained. This powder is macerated in water optionally mixed with ethanol or methanol. From this maceration, an extract is obtained, by lixiviation, and, once washed, is concentrated and then evaporated to dryness. A water-soluble powder is obtained which can be used as a solution in water or even as an aqueous-glycolic solution (butylene glycol or propylene glycol): indeed, in both cases, an identical protective effect towards peroxidative processes (inhibition of the pentane produced by a linoleic acid emulsion) is observed. Similarly, an identical protective effect on the production of pentane induced by the hydroxyl radical is observed. This dry extract can also be used as a solution in a water/glycerol mixture.

The composition according to the invention can optionally comprise an encapsulated dry extract of Chrysanthellum indicum, in an aqueous or oily continuous phase.

Needless to say, the compositions according to the invention can be in the form of simple or multiple emulsions (water/oil or oil/water creams or milks, triple emulsions, microemulsions, emulsions containing liquid crystals), aqueous or oily gels, aqueous or aqueous-alcoholic lotions, sticks or powders or any vectorized system ("controlled-release" systems or "modulated-release" systems). They can be used topically. Similarly, the extract of Chrysanthellum indicum can be an oily extract.

What is claimed is:

1. A composition for treating the effect of natural or accidental ageing of the skin, said composition comprising:

from about 0.0001% to about 0.05% by weight of a dry extract of Chrysanthellum indicum having a finite amount of flavanoids and saponosides, said composition combining an antiradical protecting action and a repairing action due to a reduced fall in the ATP content of keratynocytes after irradiations of the skin.

2. Composition according to claim 1, wherein the above-mentioned extract is a dry extract of Chrysanthellum indicum.

3. Composition according to claim 1, wherein the above-mentioned extract is an oily extract of Chrysanthellum indicum.

4. Composition according to claim 1, wherein the above-mentioned dry extract is in the form of an aqueous-glycolic solution.

5. Composition according to claim 1, wherein the above-mentioned dry extract is in the form of a solution in a water/glycerol mixture.

6. Composition according to claim 1, comprising an encapsulated extract of Chrysanthellum indicum in an aqueous or oily continuous phase.

7. Composition according to claim 1, which is simple or multiple emulsions.

8. Composition according to claim 7, which is a water/oil or oil/water cream or milk.

9. Composition according to claim 7, which is a triple emulsion, a microemulsion or an emulsion containing liquid crystals.

10. Composition according to claim 1, which is aqueous or oily gels.

11. Composition according to claim 1, which is an aqueous or aqueous-alcoholic lotion.

12. Composition according to claim 1, which is a stick.

13. Composition according to claim 1, which is a powder.

14. Composition according to claim 1, which is a controlled-release or modulated-release vectorized system.

15. Composition according to claim 1, which can be used topically.

16. Composition for care after exposure to the sun, which comprises:

| | | |
|---|---|---|
| A1 | Demineralized water | qs 100% |
| A2 | Glycerol | from 1 to 5% |
| B1 | Acrylic gelling agent | from 0.1 to 1% |
| C1 | Triethanolamine | from 0.1 to 1% |
| D1 | Antimicrobial preserving agent | from 0.5 to 1% |
| E1 | Plant oil or mineral oil | from 1 to 5% |
| F1 | Fragrance | from 0.1 to 1% |
| G1 | Butylene glycol | from 0.0025% to 1.25% |
| G2 | Dry extract of chrysanthellum | from 0.0001 to 0.05%. |

17. Composition according to claim 16, which comprises:

| A1 | Demineralized water | qs 100% |
|---|---|---|
| A2 | Glycerol | 3.00% |
| B1 | Acrylic gelling agent | 0.30% |
| C1 | Triethanolamine | 0.50% |
| D1 | Antimicrobial preserving agent | 0.55% |
| E1 | Plant oil or mineral oil | 2.00% |
| F1 | Fragrance | 0.15% |
| G1 | Butylene glycol | 0.25% |
| G2 | Dry extract of chrysanthellium | 0.01%. |

18. Anti-radical composition, which comprises:

| A1 | Sorbitol stearate | from 1 to 2% |
|---|---|---|
| A2 | Glyceryl stearate and polyethylene glycol-100 | from 2 to 5% |
| A3 | Mineral oils and plant oils | from 10 to 20% |
| B1 | Demineralized water | qs 100% |
| B2 | Propylene glycol | from 1 to 5% |
| C1 | Acrylic gelling agent | from 0.1 to 1% |
| D1 | Triethanolamine | from 0.1 to 1% |
| E1 | Antimicrobial preserving agent | from 0.5 to 1% |
| F1 | Fragrance | from 0.1 to 1% |
| G1 | Gelling agent | from 0.1 to 2% |
| H1 | Butylene glycol | from 0.0025% to 1.25% |
| H2 | Dry extract of chrysanthellium | from 0.0001 to 0.05%. |

19. Composition according to claim 18, which comprises:

| A1 | Sorbitol stearate | 1.50% |
|---|---|---|
| A2 | Glyceryl stearate and polyethylene glycol-100 | 3.25% |
| A3 | Mineral oils and plant oils | 13.50% |
| B1 | Demineralized water | qs 100% |
| B2 | Propylene glycol | 2.50% |
| C1 | Acrylic gelling agent | 0.40% |
| D1 | Triethanolamine | 0.40% |
| E1 | Antimicrobial preserving agent | 0.80% |
| F1 | Fragrance | 0.15% |
| G1 | Gelling agent | 0.70% |

-continued

| H1 | Butylene glycol | 0.50% |
|---|---|---|
| H2 | Dry extract of chrysanthellium | 0.02%. |

20. Antisun milk, which comprises:

| A1 | Demineralized water | qs 100% |
|---|---|---|
| A2 | Titanium dioxide | from 0.1 to 2% |
| A3 | Sorbitol | from 0.5 to 5% |
| B1 | Triethanoiamine | from 0.1 to 1% |
| C1 | Glyceryl stearate and polyethylene glycol-100 | from 1 to 5% |
| C2 | Glyceryl stearate | from 0.1 to 1% |
| C3 | Stearic acid | from 0.5 to 5% |
| C4 | Plant oils and mineral oils | from 5 to 15% |
| C5 | Sunscreen (cinnemate) | from 0.5 to 10% |
| C6 | Antioxidant | from 0.01 to 0.1% |
| D1 | Acrylic gelling agent | from 0.1 to 1% |
| E1 | Antimicrobial preserving agent | from 0.5 to 1% |
| F1 | Fragrance | from 0.1 to 1% |
| G1 | Butylene glycol | From 0.0025% to 1.25% |
| G2 | Dry extract of chrysanthellium | From 0.0001 to 0.05%. |

21. Antisun milk according to claim 20, which comprises:

| A1 | Demineralized water | qs 100% |
|---|---|---|
| A2 | Titanium dioxide | 0.20% |
| A3 | Sorbitol | 1% |
| B1 | Triethanolamine | 0.30% |
| C1 | Glyceryl stearate and polyethylene glycol-100 | 2.00% |
| C2 | Glyceryl stearate | 0.30% |
| C3 | Stearic acid | 1.00% |
| C4 | Plant oils and mineral oils | 8.00% |
| C5 | Sunscreen (cinnamate) | 5.00% |
| C6 | Antioxidant | 0.07% |
| D1 | Acrylic gelling agent | 0.10% |
| E1 | Antimicrobial preserving agent | 0.80% |
| F1 | Fragrance | 0.40% |
| G1 | Butylene glycol | 1.25% |
| G2 | Dry extract of chrysanthellium | 0.05%. |

* * * * *